United States Patent [19]
Richmond et al.

[11] Patent Number: 5,020,562
[45] Date of Patent: Jun. 4, 1991

[54] MULTILINE CHECK VALVE ASSEMBLY

[75] Inventors: Frank M. Richmond, Harvard, Ill.; Timothy Vanderveen, Poway; Rick Kimes, Carlsbad, both of Calif.

[73] Assignee: IMED Corporation, San Diego, Calif.

[21] Appl. No.: 565,257

[22] Filed: Aug. 9, 1990

Related U.S. Application Data

[63] Continuation-in-part of Ser. No. 441,954, Nov. 28, 1989.

[51] Int. Cl.$^5$ ............................................. F16K 15/18
[52] U.S. Cl. ..................................... 137/15; 137/606; 251/149.1; 604/80; 604/247
[58] Field of Search ................. 137/15, 522, 523, 605, 137/606, 614.05, 843, 852, 854, 901; 251/149.1, 149.7; 604/80, 83, 247, 249

[56] References Cited

U.S. PATENT DOCUMENTS

| | | | |
|---|---|---|---|
| 2,973,718 | 3/1961 | Deutsch | 137/606 |
| 3,385,301 | 5/1968 | Harautuneian | 137/843 X |
| 3,831,629 | 8/1974 | Mackal et al. | |
| 4,210,173 | 7/1980 | Choksi et al. | 137/854 X |
| 4,506,691 | 3/1985 | Tseo | 137/606 X |
| 4,666,429 | 5/1987 | Stone | 604/83 |
| 4,681,132 | 7/1987 | Lardner | 137/843 X |
| 4,762,149 | 8/1988 | Pickl | 137/854 X |

OTHER PUBLICATIONS

Brochure, L&W Technology, Inc., "Use the SAFE-PORT TM ... In the SAFE MULTIPORT TM," (no date).
Brochure, L&W Technology, Inc., "Finally ... The SAFE MULTIPORT TM", (no date).

*Primary Examiner*—Stephen M. Hepperle
*Attorney, Agent, or Firm*—Nydegger & Associates

[57] ABSTRACT

A multiline check valve assembly has an elongated body which defines a fluid passageway and which is formed with a plurality of valve cavities that are in fluid communication with the fluid passageway. Each valve cavity has a resilient valve element disposed within the cavity and each valve element rests in the cavity with one end against a protrusion disposed in the cavity for centering the element within the cavity. The resilient valve element is biased to urge its other end against a valve seat that surrounds an opening to the valve cavity to create a fluid tight seal with the valve seat and close the opening. In addition, an access port is formed circumferentially around both the valve seat and opening to establish a fluid communication path through the access port to the fluid passageway in the body when the valve element is separated from the valve seat. Specifically, when an appropriate fluid line connector is inserted into the access port to urge against the resilient valve element, the valve element is deformed away from the valve seat to complete the fluid communication path between the access port and the fluid passageway. In an alternate embodiment, the body of the valve is substantially cube-shaped and has a plurality of valve cavities disposed transversely therein, each of the valve cavities being in fluid communication with the fluid passageway that is formed by the valve body.

16 Claims, 3 Drawing Sheets

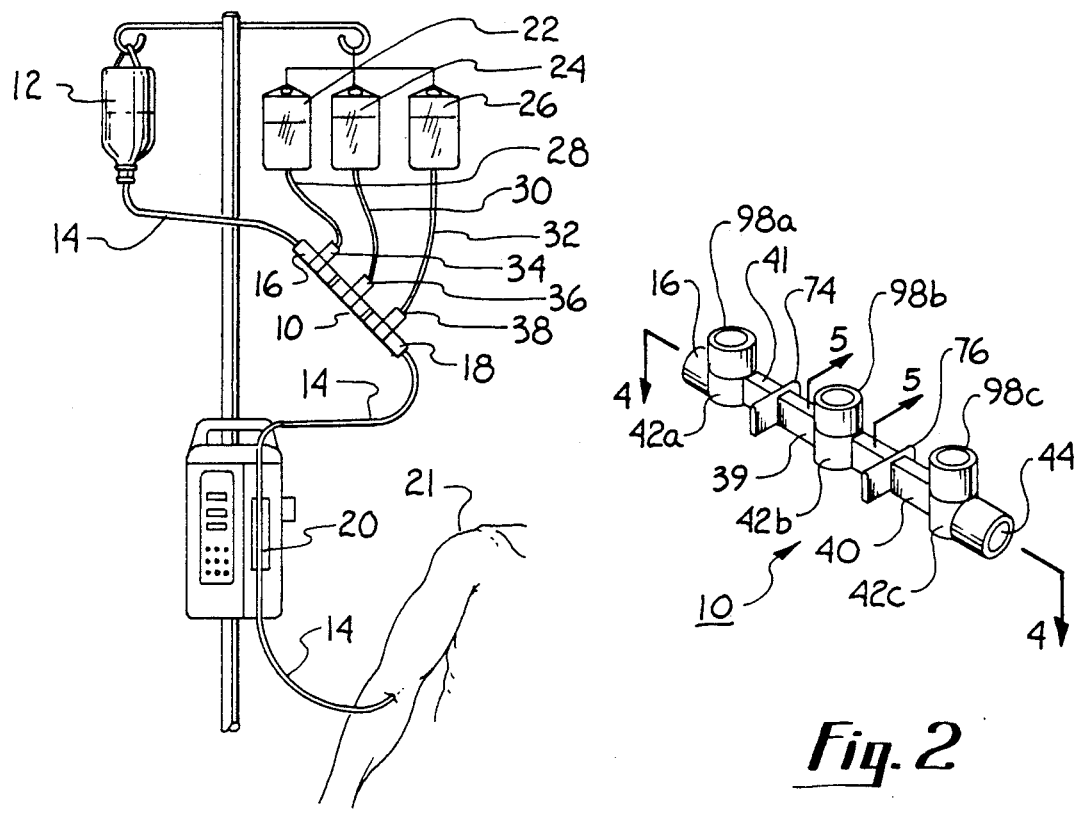
Fig. 1
Fig. 2
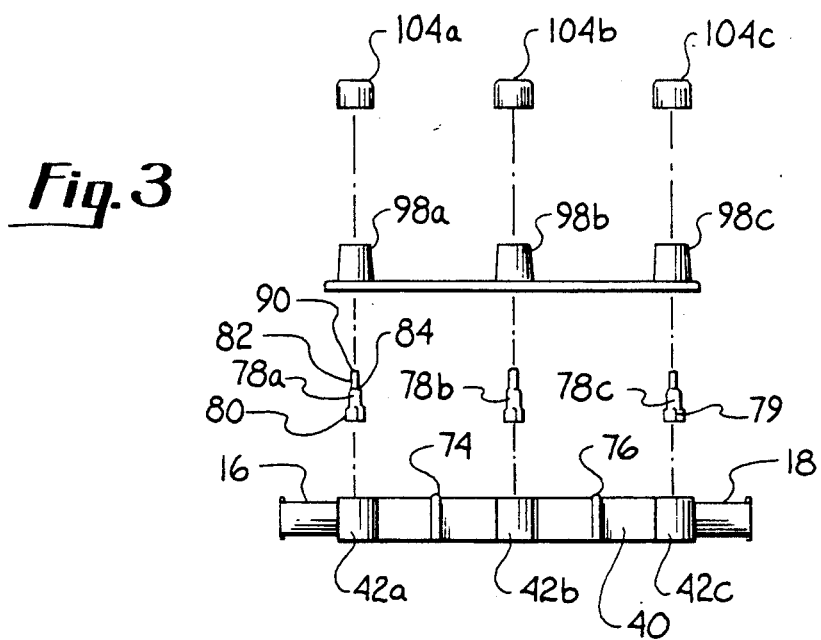
Fig. 3

MULTILINE CHECK VALVE ASSEMBLY

FIELD OF THE INVENTION

This application is a continuation-in-part of co-pending application Ser. No. 441,954, filed Nov. 28, 1989.

The present invention relates generally to a check valve assembly. More specifically, the present invention relates to check valve assemblies which may be interconnected between a primary fluid passageway and a plurality of secondary fluid sources. The present invention is particularly, though not exclusively, useful for infusing fluids into a patient from several sources through a single IV administration line.

BACKGROUND OF THE INVENTION

The use of volumetric pumps to assist in the infusion of medications to patients is well established in the medical field. Several devices have been proposed for this purpose. For example, U.S. Pat. No. 3,985,133, which issued to Jenkins, claims and discloses a volumetric pump that accurately infuses medications to a patient. As another example, U.S. Pat. No. 4,617,014 to Cannon discloses a linear peristaltic pump which also accurately infuses medications to a patient. Such systems, however, are typically designed for the infusion of medications through a single fluid line. Thus, whenever an additional medical fluid needs to be infused, either the pump must be temporarily shut down while the fluid container in the existing IV system is changed or a separate IV system must be set up. In either case, there may be unacceptable delays. Moreover, additional IV lines may need to be inserted into the patient, causing patient discomfort and compounding the problems associated with IV line management and maintenance. Such problems, however, can be avoided if the new medical fluid can be introduced into the existing fluid delivery system without disassembling the existing system.

Several valving devices have been proposed in the prior art for diverting fluid flow from one path to another. One such valve is the manually-operable three-way valve device disclosed in U.S. Pat. No. 3,057,370 to Hamilton. Other valves, such as the check valve disclosed in U.S. Pat. No. 3,352,531 to Kilmark have been proposed which are opened by cooperation with an external structure, such as the tip of a syringe, to establish a fluid passageway. Additional examples of such devices in the medical field are U.S. Pat. No. 3,385,301 to Harautuneian and U.S. Pat. No. 3,799,171 to Patel. Another depressor activated device is the valve disclosed in U.S. Pat. No. 3,965,910 to Fischer which defines a separate passageway for the addition of a second fluid into an existing fluid pathway during engagement of the depressor. Further, these are numerous examples of so-called piggy back systems which allow for the continuity of infusion from two separate fluid sources. The device disclosed in U.S. Pat. No. 4,533,347 to Deckert and assigned to the same assignee as the present invention is an example of one such system. There is, however, still the need for continuity of infusion from more than one secondary source. Also, there is a need for an automatic return to the normal fluid flow of the pre-existing fluid pathway when flow from several fluid sources has been completed.

Accordingly, it is an object of the present invention to provide a multiline check valve which is simple in operation and allows for easy engagement of a plurality of secondary fluid sources into a pre-existing fluid flow line. Another object of the present invention is to provide a cost effective disposable valve for use with a pumping system that will permit the accurate delivery of fluid from a plurality of separate fluid sources. It is still another object of the present invention to provide a valve which can re-establish the pre-existing fluid pathway after the introduction of fluid from the second sources has been completed.

SUMMARY OF THE INVENTION

The preferred embodiment of the novel multiline check valve assembly in accordance with the present invention comprises an elongated body which defines a longitudinal fluid passageway. Additionally, the body has a plurality of serially aligned cylindrical-shaped valve cavities which are formed in the body. These cavities are formed generally transverse to the fluid passageway and in fluid communication with the fluid passageway. Specifically, each valve cavity has an inlet from the passageway and an outlet to the passageway which together allows for fluid flow through the valve cavity. Within each valve cavity are four ribs, which are formed on the walls of the cavity in an orientation that is substantially perpendicular to the direction of fluid flow through the passageway. More particularly, one pair of ribs is formed immediately adjacent to the passageway inlet to the cavity with the ribs disposed on opposite sides of the inlet from each other. Similarly, the other pair of ribs is formed on the cavity's inside wall immediately adjacent to the passageway outlet. Again the ribs are disposed on opposite sides of the outlet from each other. The bottom wall of the cavity is formed with a raised protrusion and the top of the valve cavity is formed with a valve seat which surrounds and defines an opening.

Disposed within each valve cavity is a resilient valve element which has one end that straddles the protrusion of the valve cavity and has its other end positioned to urge against the valve seat. More particularly, each valve element is formed with a skirt section that defines a recess. This recessed portion of the valve element skirt is insertable over the protrusion of the valve cavity to center the valve element within the valve cavity. In order to create a fluid seal, the valve element is formed with a shoulder which normally rests against the valve seat. Further, the valve element has a portion which extends through the opening circumscribed by the valve seat. In the preferred embodiment, this extended portion projects into an access port which is formed on the valve body around the valve seat. The access port thereby provides for an engagement between the valve body and an appropriate fluid line connector to establish fluid communication between a secondary fluid source and the fluid passageway in the valve body.

For the operation of the check valve assembly, it is to be appreciated that the resilient valve element is normally biased into a first, or seated, configuration wherein a fluid seal is established between the shoulder of the valve element and the valve seat. When a fluid line connector is inserted into the access port, however, the connector urges against the extended portion of the valve element to deform the valve element into its second, or unseated, configuration. In this second configuration, the shoulder of the valve element is seperated from the valve seat to establish a fluid communication pathway between the fluid passageway in the valve body and a secondary fluid source which is in fluid communication with the connector. When the valve element is so deformed, it may happen that the ribs of the valve cavity contact the deformed valve element to prevent occlusion of the fluid passageway inlet or outlet by the deformed valve element.

For the purposes of the present invention, the valve body may either be of unitary construction or, preferably, may be formed by the attachment of a top plate onto a base portion. With the configuration wherein a top plate is joined to a base, the valve cavities and the interconnecting fluid passageway are formed in the base. Also, with this configuration, the access ports are formed on the top plate. When the top plate and base are joined, there is a mating engagement of the access ports with the valve cavities.

In an alternate embodiment of the check valve assembly, the valve body is substantially cube-shaped. In this embodiment, the cubic body can be integrally formed, or can be formed by connecting together two or more subassemblies, through the center of each of which extends a fluid passageway. Adjacent subassemblies are juxtaposed such that the respective fluid passageways of the adjacent subassemblies are positioned end-to-end to form a single continuous fluid passageway through the valve body. The valve body is thus established by connecting together the respective subassemblies.

Importantly, each subassembly has two substantially parallel but oppositely oriented valves. The valve cavities of each subassembly are formed transverse to the fluid passageway and in fluid communication with the fluid passageway. More particularly, the fluid passageway of each respective subassembly extends through each of the valve cavities of the subassembly substantially intermediate the access port and bottom wall of each respective cavity. The valve cavities of each subassembly are positioned side-by-side, with the individual cavities being positioned in the subassembly in 180° orientations to each other. In turn, a plurality of valve bodies may be connected together in fluid communication by connecting together the respective fluid passageways of the valve bodies.

The novel features of this invention, as well as the invention itself, both as to its structure and its operation, will be best understood from the accompanying drawings, taken in conjunction with the accompanying description, in which similar reference characters refer to similar parts, and in which:

BRIEF DESCRIPTION OF THE DRAWINGS

FIG. 1 is a front elevational view of the novel multiline valve assembly in its intended environment;

FIG. 2 is a perspective view of the novel multiline valve assembly;

FIG. 3 is an exploded side view of the novel multiline valve assembly;

DESCRIPTION OF THE PREFERRED EMBODIMENT

Figure 4:
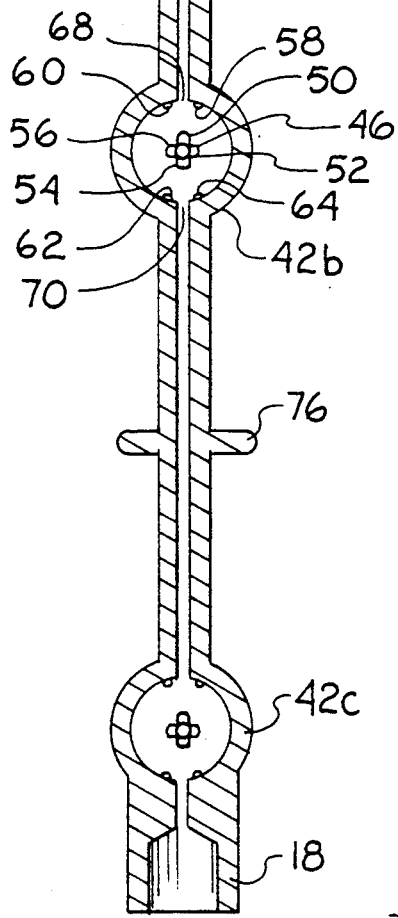
FIG. 4 is a top cross-sectional view of the body portion of the novel multiline valve assembly as seen along the line 4—3 in FIG. 2.

Referring initially to FIG. 1, a multiline valve assembly 10 is shown operatively connected in fluid communication between a primary fluid source 12 and an IV infusion pump 20 through a line 14. More particularly, fittings 16 and 18 permanently or detachably connect the assembly 10 with the line 14. For purposes of the present invention, any suitable IV infusion pump 20 may be operatively connected with line 14 downstream of multiline valve assembly 10 for infusing fluid which passes through multiline valve assembly 10 into a patient 21. Also shown connected to assembly 10 are a plurality of secondary fluid sources 22, 24, and 26, which are respectively attached to assembly 10 through lines 28, 30, and 32 by fittings 34, 36, and 38, respectively. It will be understood by the skilled artisan that the fittings 16, 18, 28, 30, and 32 are preferably standard luer IV fittings and that fittings 16 and 18 may interchangeably be either male or female fittings.

The overall structure of valve assembly 10 can perhaps be best appreciated with reference to both FIG. 2 and FIG. 3. In FIG. 2 it is seen that valve assembly 10 has an elongated valve body 39 which is established by joining a base 40 with a top plate 41 by any means well known in the art, such as by solvent bonding, sonic sealing, or RF sealing. As shown, a series of valve cavities 42a, b and c are formed along the valve body 39 and a fluid passageway 44 is established longitudinally within the valve body 39. To allow fluid flow through valve assembly 10, fluid passageway 44 is in fluid communication with each of the valve cavities 42a, b, and c.

In FIG. 4 it is seen that each cavity 42 of valve assembly 10 is formed with a centering protrusion 46. As seen by cross referencing FIG. 4 with FIG. 5 or FIG. 6, each protrusion 46, is elevated with respect to the bottom 48 of the cavity 42, and includes radial ledges 50, 52, 54, and 56 which extend from the centering protrusion 46. Like protrusion 46 the radial ledges 50, 52, 54 and 56 are elevated relative to bottom 48 of valve cavity 42. Using cavity 42b as an example, FIG. 4 also shows four longitudinal ribs 58, 60, 62, and 64, which are formed on the walls 66 of valve cavity 42b. More particularly, the ribs 58, 60, are formed immediately adjacent to the cavity inlet 68 while ribs 62, 64 are formed immediately adjacent to the cavity outlet 70 of fluid passageway 44. All ribs 58, 60, 62 and 64 protrude from walls 66 into valve cavity 42b. It will be further appreciated in cross-reference to FIGS. 5 and 6 that ribs 58, 60, 62, 64, as well as cavity inlets 68, 70, extend from the bottom 48 of valve cavity 42 to the top 72 of valve cavity 42. If desired, ribs 58, 60, 62, 64 or inlets 68, 70 could extend only part way between bottom 48 and top 72 of cavity 42.

Referring back to FIG. 2, it may be seen that base 40 may also be formed with stand off adaptors 74 and 76 for facilitating engagement between multiline valve assembly 10 and other appropriate IV infusion system components as required. Finally, it will be appreciated that the base 40, as well as the other components of multiline valve assembly 10, may be composed of any suitable material, such as lightweight plastic. Importantly, the selected material should both be structurally strong, and compatible with the fluid medicament being infused.

Figure 5:
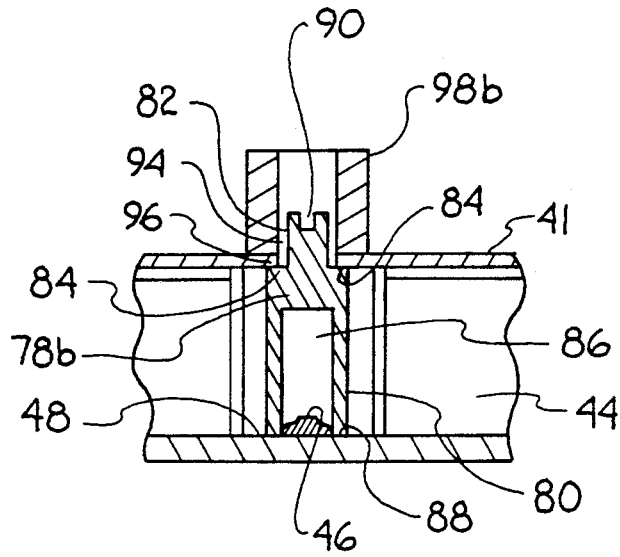
FIG. 5 is a cross-sectional view of one valve cavity as seen along the line 5—5 in FIG. 2, with the valve element in its seated configuration.

The interaction of components of valve assembly 10 is best indicated in FIG. 3, which shows a plurality of resilient valve elements 78a, b and c that are respectively positioned in each of the valve cavities 42a, b and c. Each of the valve elements 78a, b and c, as seen in FIGS. 3 and 5, is formed with a hollow skirt portion 80 and an extension 82. Further, each valve element 78a, b and c is formed with a seating shoulder 84 located between skirt portion 80 and extension 82. Additionally, with specific regard to valve cavity 42b, skirt portion 80 forms a recess 86 (shown in cross-section in FIG. 5) which establishes an interference fit between valve element 78b and protrusion 46 in valve cavity 42b. Specifically, the recess 86 is positioned in a surrounding relationship with the centering protrusion 46 and is positioned for an interference fit with the radial ledges 50, 52, 54, 56. When so positioned, it will be understood that the bottom edge 88 of valve element 78 rests against the bottom 48 of valve cavity 42. As will readily be appreciated, this disposition of valve element 78a, b and c around their respective centering protrusions 46 substantially centers each valve element 78a, b and c within a respective valve cavity 42a, b and c.

It is also seen in reference to FIG. 2 that the extension 82 of valve element 42 may be formed with a groove 90. In addition, each valve element 78a, b and c may be formed with a plurality of ridges 79 which extend longitudinally along the skirt 80 of the valve element 78a, b and c. Finally, the material of valve element 78a, b and c is selected to be resilient and deformable, so that it regains its non-deformed shape shown in FIGS. 3 and 5 upon removal of any deforming force. For the embodiment shown in FIG. 2, valve element 42 is composed of an elastomeric material well known in the art, such as rubber.

Figure 6:
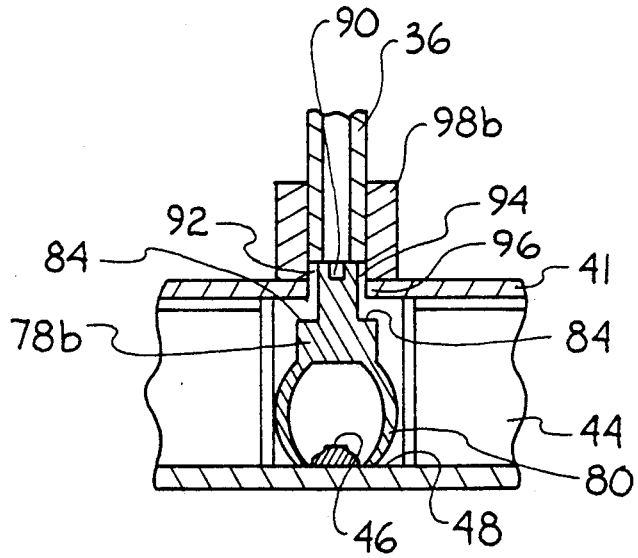
FIG. 6 is a cross-sectional view of the valve cavity as seen in FIG. 5, with the valve element in its unseated configuration.

FIGS. 2 and 3 also show that while valve body 39 may be of unitary construction, preferably, a top plate 41 and base 40 are formed as a separate components of multiline valve assembly 10. When formed as a separate component of assembly 10, top plate 41 may be attached to base 40 by any suitable means, such as by gluing, solvent bonding or sonic welding, to cover the passageway 44 formed through valve body 39. In either case, top plate 41 is formed with a plurality of openings 94, which are each circumscribed by a valve seat 96 for forming a fluid tight seal with the respective shoulders 84 of associated valve elements 78. More specifically, each valve element 78 is biased to its seated or non-deformed configuration, as shown in FIG. 5, wherein shoulder 84 is disposed in fluid sealable contact around the circumference of its associated valve seat 96 to prevent fluid communication through the respective opening 94. While shoulder 84 and seat 96 are shown in FIG. 5 to be substantially parallel to the dimension of elongation of assembly 10, it will be understood that the shoulder 84 (and, correspondingly, seat 96) may be tapered relative to the dimension of elongation of assembly 10. It may now be appreciated that by forming valve element 78 of a resilient material, valve element 78 may be deformed from its seated configuration described above to an unseated or deformed configuration wherein shoulder 84 is distanced from its associated valve seat 96. Such a deformed configuration is shown in FIG. 6. As shown, when valve element 78a, b or c is deformed, a pathway 92 is established through opening 94 which permits fluid communication through top plate 41 into fluid passageway 44.

FIG. 2 also shows access ports 98a, b and c extending respectively from each opening 94 to receive the appropriate fitting 34, 36, or 38 shown in FIG. 1. With fitting 34, 36 or 38 properly engaged with access ports 98a, b or c, a fluid communication pathway 92 is established between the associated secondary fluid source 22, 24, or 26 and the fluid passageway 44. This connection is best seen in FIG. 6. Finally, FIG. 3 shows a plurality of removable covers 104a, b and c that protect access port 98a, b and c when multiline valve apparatus 10 is not in use. It will therefore be appreciated that the covers 104 keep dirt and other material from entering multiline valve assembly 10 when assembly 10 is not in use. Additionally, covers 104 are preferably of any suitable tamperproof construction.

Figure 7:
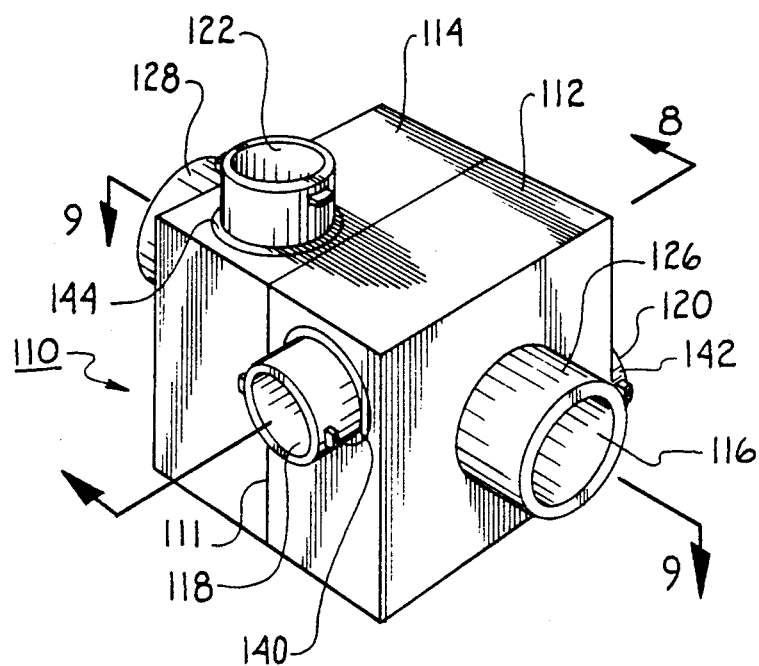
FIG. 7 is a perspective view of an alternate embodiment of the novel multiline check valve assembly.
Figure 8:
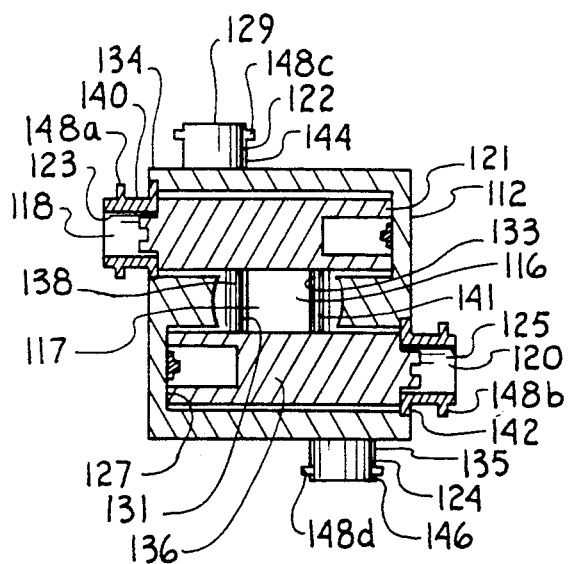
FIG. 8 is a cross-sectional view of the check valve assembly as seen along the line 8—8 in FIG. 7.
Figure 9:
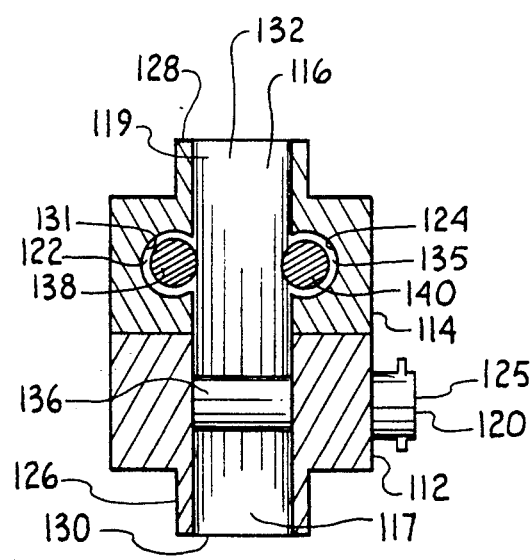
FIG. 9 is a cross-sectional view of the check valve assembly as seen along the line 9—9 in FIG. 7.

Turning now to FIGS. 7, 8, and 9, an alternate embodiment of multiline valve assembly 10 is shown, generally designated 110. Assembly 110 is shown to have a valve body 111. Body 111 includes a subassembly 112, a subassembly 114, and a fluid passageway 116 which is formed by positioning respective fluid passageways 117, 119 (shown in FIG. 9) of subassemblies 112, 114 end-to-end. Subassemblies 112, 114 are attached together by any means well known in the art, such as by solvent bonding, sonic bonding or rf sealing. It is to be understood, however, that body 111 could be formed as a single integral structure with a single continuous passageway formed therethrough.

Each of the subassemblies 112, 114 is further shown to include two valve cavities which are transversely oriented with the respective fluid passageways of the subassemblies 112, 114. More particularly, as shown in FIGS. 8 and 9, subassembly 112 includes valve cavities 118, 120 which are formed in subassembly 112 in a 180° orientation relative to each other. As shown, cavities 118, 120 are each transversely oriented to passageway 117 and are in fluid communication with passageway 117. Passageway 117 extends through the cavities 118, 120 substantially intermediate the respective bottom 121, opening 123 of cavity 118 and opening 125, bottom 127 of cavity 120. As shown, openings 123, 125 are formed by attaching (e.g., by ultrasonically welding) respective cap portions 140, 142 onto body 111. The cap portions 140, 142 are respectively in coaxial alignment with cavities 118, 120. Similarly, the subassembly 114 includes valve cavities 122, 124 which are formed in subassembly 114 in a 180° relationship to each other and which are transverse to passageway 119. Passageway 119 extends through the cavities 122, 124 substantially intermediate the respective opening 129, bottom 131 of cavity 122 and bottom 133, opening 135 of cavity 124. Openings 129, 135 are respectively formed by cap portions 144, 146, which are in all essential respects identical to cap portions 140, 142. Each of the cap portions 140, 142, 144, 146 is shown to include respective luer ears 148a–d, for engagement with an appropriate luer fitting. As shown in FIGS. 7, 8, and 9, the subassemblies 112, 114 are orthogonally oriented with respect to each other, i.e., with cavities 118, 120 of subassembly 112 perpendicular to cavities 122, 124 of subassembly 114. It is to be understood that each valve cavity 118, 120, 122, 124 is in all essential respects identical in construction and operation to the cavity 42 previously disclosed. Moreover, each cavity 118, 120, 122, 124 has a respective valve element 134, 136, 138, 141 disposed therein. It is also to be understood that each valve element 134, 136, 138, 141 is in all essential respects identical in construction and operation to valve element 78b.

If desired, one of the cavities 118, 120, 122, or 124 could be modified to provide a means for mounting assembly 110 to a suitable surface, such as an IV pole or a pump handle (not shown). In accordance with the above disclosure, it is to be appreciated that a relatively compact configuration of assembly 110 is effected by disposing the valve cavities within their respective subassembies substantially transverse to passageway 116, as shown. It is to be further appreciated that each subassembly 112, 114 may be integrally formed (e.g., by molding) with more than two valve cavities, and that assembly 110 may comprise a greater number of subassemblies 112, 114, as desired. For example, as perhaps best appreciated in reference to FIG. 7, passageway 116 could be lengthened by positioning a third subassembly (not shown) adjacent either of the subassemblies 112, 114 (with the respective valve cavities of the third subassembly in fluid communication with passageway 116) without departing from the scope of the present invention.

Still referring to FIGS. 7 and 9, the fluid passageway 116 is shown to include an end 126 and an opposite end 128, which is placed in fluid communication with end 126 through passageway 116. Ends 126, 128 define respective openings 130, 132. The ends 126, 128, may be any suitable connectors, such as respective male and female luer fittings.

OPERATION

In the operation of the novel multiline valve assembly 10, reference is initially made to FIGS. 1 and 2 where it is seen that multiline valve assembly 10 is attached to line 14 through fittings 16, 18, respectively. In this configuration, a single path for fluid communication between primary source 12 and pump 20 exists through passageway 44. Furthermore, in reference to FIG. 5, it may be seen that when no secondary fluid source is attached to an access port 98a, b or c, the respective valve element 78a, b or c is biased into its undeformed, or seated, configuration. As seen in FIG. 5, when valve element 78 is in this seated configuration, its shoulder 84 forms a fluid tight seal around the valve seat 96 of top plate 41, thereby preventing fluid communication into fluid passageway 44 through opening 94. When cover 104 is removed, however, and a secondary fluid source (e.g., source 24) is attached to multiline valve assembly 10 as shown in FIG. 6, the respective secondary fitting (e.g., fitting 36) extends into access port 98b and urges against the extension 82 of valve element 78b. By so urging, the fitting 36 deforms valve element 78b into its unseated or deformed configuration, wherein a fluid pathway 92 is formed through opening 94 to connect secondary source 22 in fluid communication with fluid passageway 44. Alternatively, it is to be understood that resilient valve element 78b may be constructed to deform, if desired, when fluid pressure from source 22 acts against extension 82 and shoulder 84 of resilient valve element 78b. In either case, it may now be appreciated that when valve element 78b is so deformed, one or more of the ribs 58, 60, 62, 64 may contact skirt portion 80 of valve element 78 to preclude occlusion of inlet 68 or outlet 70 by valve element 78. Thus, fluid passageway 44 remains unoccluded to permit fluid communication between primary source 12 and pump 20 when valve element 78b is in its deformed configuration to simultaneously connect fluid source 24 in fluid communication with pump 20.

It is to be appreciated that, although the disclosure here has focused primarily on the structure and interaction of valve cavity 42b and valve element 78b, the structure and interaction of valve cavities 42a and c with valve elements 78a and c are in all essential aspects equivalent.

In the operation of the alternate embodiment of assembly 110, reference is made to FIGS. 7, 8, and 9. It is to be appreciated that ends 126, 128 of assembly 110 may be attached to the IV line 14 shown in FIG. 1 by means of any appropriate connector, such as a male or female luer fitting, respectively. Then, one or more fluid sources, such as the sources 22, 24, 26, may be placed in fluid communication with the cavities 118, 120, 122, and 124 (and, accordingly, with passageway 116) through appropriate IV lines. It will be understood that the subsequent operation of assembly 110 will, in all substantial respects, be identical with the operation of multiline valve assembly 10 previously disclosed.

While the particular multiline valve assembly as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

We claim:

1. A valve assembly connecting the lines of a plurality of secondary fluid sources in fluid communication with a primary IV infusion line which comprises:
    a valve body defining a central fluid passageway and having a plurality of valve cavities disposed in said body transverse to said passageway, said valve cavities each having a bottom and an opening spaced from said bottom, said openings having respective valve seats circumscribing said openings, each of said valve cavities being in fluid communication with said passageway intermediate respective said opening and said bottom, each of said bottoms being distanced from said passageway;
    resilient valve elements disposed in respective said valve cavities between respective said bottoms and respective said openings, said valve elements being individually deformable between first configurations wherein said valve elements are in fluid sealable contact with respective said valve seats to occlude respective said openings and second configurations wherein said valve elements are distanced from respective said seats to establish respective fluid pathways through respective said openings into said passageway; and
    means projecting from respective said bottoms of said valve cavities and engageable with respective said valve elements for substantially centering respective said valve elements within said respective valve chambers.

2. A valve assembly as recited in claim 1 wherein each of said valve elements has a skirt defining a recess, and said projecting means comprises protrusions for engaging said recesses of said valve elements to center and orient said elements in said cavities.

3. A valve assembly as recited in claim 2 wherein each of said valve bodies comprises a top plate and a base portion, said opening being formed on said top plate, said top plate having an access port circumferentially surrounding said valve seat and said opening for receiving said line from said secondary source.

4. A valve assembly as recited in claim 3 wherein each of said valve elements is formed with a shoulder for sealable contact with respective said valve seat of said valve element, each of said valve elements being further formed with an extension insertable into respective said access port which extends from said shoulder opposite said skirt.

5. A valve assembly as recited in claim 4 wherein each of said valve elements is biased into said first configuration and deformable into said second configuration.

6. A valve assembly as recited in claim 5 wherein each of said valve elements is deformable into said second configuration by fluid pressure.

7. A valve assembly as recited in claim 5 wherein each of said valve elements is deformable into said second configuration by respective said lines from respective said secondary sources.

8. An assembly for permitting the infusion of fluid into an IV line which comprises:
  a base which defines a fluid passageway connected in fluid communication with said IV line;
  a plurality of access ports mounted on said base, each of said access ports having a valve seat and defining a fluid pathway in fluid communication with said fluid passageway each of said fluid pathways being transverse to said fluid passageway, said fluid passageway extending through each of said fluid pathways substantially intermediate each of said pathways;
  deformable means operably associated with each of said access ports, each of said deformable means having a first end positioned against said base and having a second end urging against each of said respective valve seats to block said fluid pathways when said deformable means are in a first configuration and to urge against said valve seats to open said fluid pathways when said deformable means are in a second configuration to distance said deformable means from said valve seat; and
  means on said base to hold said first ends of said deformable means stationary relative to said base.

9. An assembly as recited in claim 8 wherein each of said fluid pathways is defined by a respective valve cavity, said valve cavities being formed with respective openings surrounded by respective valve seats, each of said openings being in fluid communication with its respective said access port and each of said valve cavities also being formed with means for centering each of said respective deformable means within said respective valve cavity.

10. An assembly as recited in claim 9 wherein each of said deformable means comprises a resilient valve element disposed in its respective said valve cavity, each of said valve elements being deformable between said first and second configurations.

11. An assembly as recited in claim 10 further comprising a protrusion formed on each respective said valve cavity opposite each respective said valve seat for engaging each of said respective recesses of said respective valve elements to center and orient respective said elements in respective said cavities.

12. An assembly as recited in claim 10 wherein each of said valve elements is formed with a shoulder for forming a fluid sealable contact with its respective said valve seat, each of said valve elements being further formed with an extension insertable into respective said access port which extends from respective said shoulder opposite respective said skirt.

13. An assembly as recited in claim 10 wherein each of said valve elements is biased into said first configuration, and deformable into said second configuration.

14. An assembly as recited in claim 10 wherein each of said valve elements is deformable into said second configuration by fluid pressure.

15. An assembly as recited in claim 10 wherein each of said valve elements is deformable into said second configuration by inserting a fitting into respective said opening to urge against respective said valve element.

16. A method for infusing fluid from a plurality of secondary sources into an IV line which is carrying fluid from a primary source, which comprises the steps of:
  (a) engaging said primary source in fluid communication with a device comprising:
    a valve base defining a central fluid passageway and having a plurality of valve cavities disposed in said base transverse to said passageway, said valve cavities each having a bottom and an opening spaced from said bottom, said openings having respective valve seats circumscribing said openings, each of said valve cavities being in fluid communication with said passageway intermediate respective said opening and said bottom each of said bottoms being distanced from said passageway;
    resilient valve elements disposed in respective said valve cavities between respective said bottoms and respective said openings, said valve elements being individually deformable between first configurations wherein said valve elements are in fluid sealable contact with respective said valve seats to occlude respective said openings and second configurations wherein said valve elements are distanced from respective said seats to establish respective fluid pathways through respective said openings into said passageway; and
    means projecting from respective said bottoms of said valve cavities and engageable with respective said valve elements for substantially centering respective said valve elements within respective valve chambers; and
  (b) inserting a plurality of adaptors connected in fluid communication with respective said secondary sources into respective said openings to deform respective said valve elements into said second configurations to thereby establish a respective plurality of fluid pathways between respective said secondary sources and said fluid passageway.

* * * * *